United States Patent [19]

Osborne et al.

[11] Patent Number: 5,208,162

[45] Date of Patent: May 4, 1993

[54] METHOD AND APPARATUS FOR MONITORING CORROSION

[75] Inventors: Michael W. Osborne, Lilburn; William G. England, Suwanee, both of Ga.; Xiuyi Zhang, Shandong, China

[73] Assignee: Purafil, Inc., Doraville, Ga.

[21] Appl. No.: 812,766

[22] Filed: Dec. 23, 1991

Related U.S. Application Data

[63] Continuation-in-part of Ser. No. 521,079, May 8, 1990, abandoned, and a continuation of PCT U.S. Ser. No. 91/03097, May 6, 1991.

[51] Int. Cl.$^5$ .............................................. G01N 17/02
[52] U.S. Cl. ........................................ 436/6; 436/151; 422/53; 422/93; 422/98; 73/24.01; 73/86; 324/71.2
[58] Field of Search ................. 422/53, 82.01, 93, 98; 436/6, 61, 151; 73/86, 24.01, 580, 579, DIG. 1; 324/71.1, 71.2; 310/312

[56] References Cited

U.S. PATENT DOCUMENTS

| | | | |
|---|---|---|---|
| 3,253,219 | 5/1966 | Littler | 422/53 |
| 4,282,181 | 8/1981 | Pierce | 422/53 |
| 4,338,563 | 7/1982 | Rhoades et al. | 324/65 CR |
| 4,514,681 | 4/1985 | Finley et al. | 324/65 CR |
| 4,539,846 | 9/1985 | Grossman | 422/53 |
| 4,587,479 | 5/1986 | Rhoades et al. | 324/65 CR |
| 4,755,744 | 7/1988 | Moore et al. | 324/65 CR |
| 4,783,987 | 11/1988 | Hager et al. | 73/32 A |
| 4,808,538 | 2/1989 | Roffey et al. | 422/53 X |
| 4,869,874 | 9/1989 | Falat | 422/53 |

OTHER PUBLICATIONS

Instrument Society of America, Standard Environmental Conditions for Process Measurement and Control Systems: Airborne Contaminants, pp. 2-15 (1985), Research Triangle Park, N.C. 27709.

Rohrback Cosasco Systems, Inc., Model CK-3 Corrosometer Instrument, 2 pages.

Corrosion Monitoring Equipment, Systems and Services, pp. 4-7.

Model 610 High Sensitivity Atmospheric Corrosion Sensor, 2 pages.

Maxtek, Inc. Thin Film Products, 4 pages (1987).

Primary Examiner—James C. Housel
Assistant Examiner—Jeffrey R. Snay
Attorney, Agent, or Firm—Jones & Askew

[57] ABSTRACT

A method and apparatus for using a coated piezoelectric crystal to monitor and report corrosion in terms recognized as conforming to an industry standard is disclosed. The present invention provides a method of and system for monitoring corrosion in a corrosive atmosphere, comprising and carrying out the steps of exciting in the atmosphere a crystal, coated with a corrodible metallic substance and having a known vibration frequency; measuring the change in the frequency of vibration resulting from corrosion of the corrodible substance during each of a plurality of intervals of time, including a reference interval and at least one subsequent measurement interval; generating a thickness signal representing the thickness of corrosion corresponding to the measured change in frequency during the measurement interval; and converting the corrosion thickness signal for the measurement interval to a reference signal representing the thickness of corrosion accumulated during the reference interval. The invention also preferably includes correcting the measured frequency change during each interval to account for any deviation in the temperature in the atmosphere from a preset standard temperature. The present invention also preferably includes a humidity sensor, which serves as the impetus for providing an alarm to the user if the relative humidity is above a preset limit, or if the relative humidity changes during an interval by more than a preset limit. A corrosion monitor according to the present invention finds application in such environments as industrial process measurement and control rooms, motor control centers, electrical rooms, semiconductor clean rooms, electronic fabrication sites, commercial data centers, museums, libraries, and archival storage rooms.

21 Claims, 6 Drawing Sheets

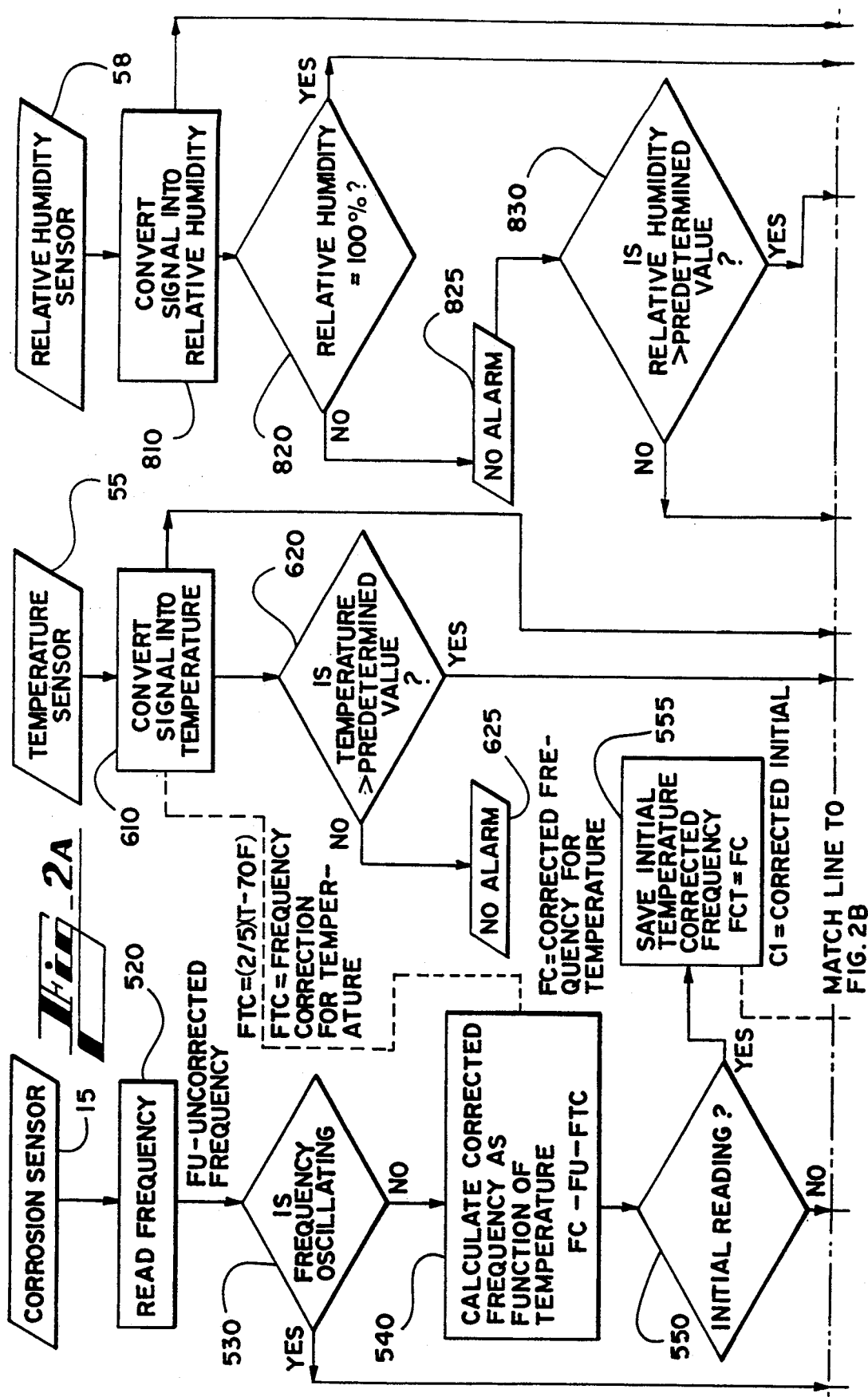

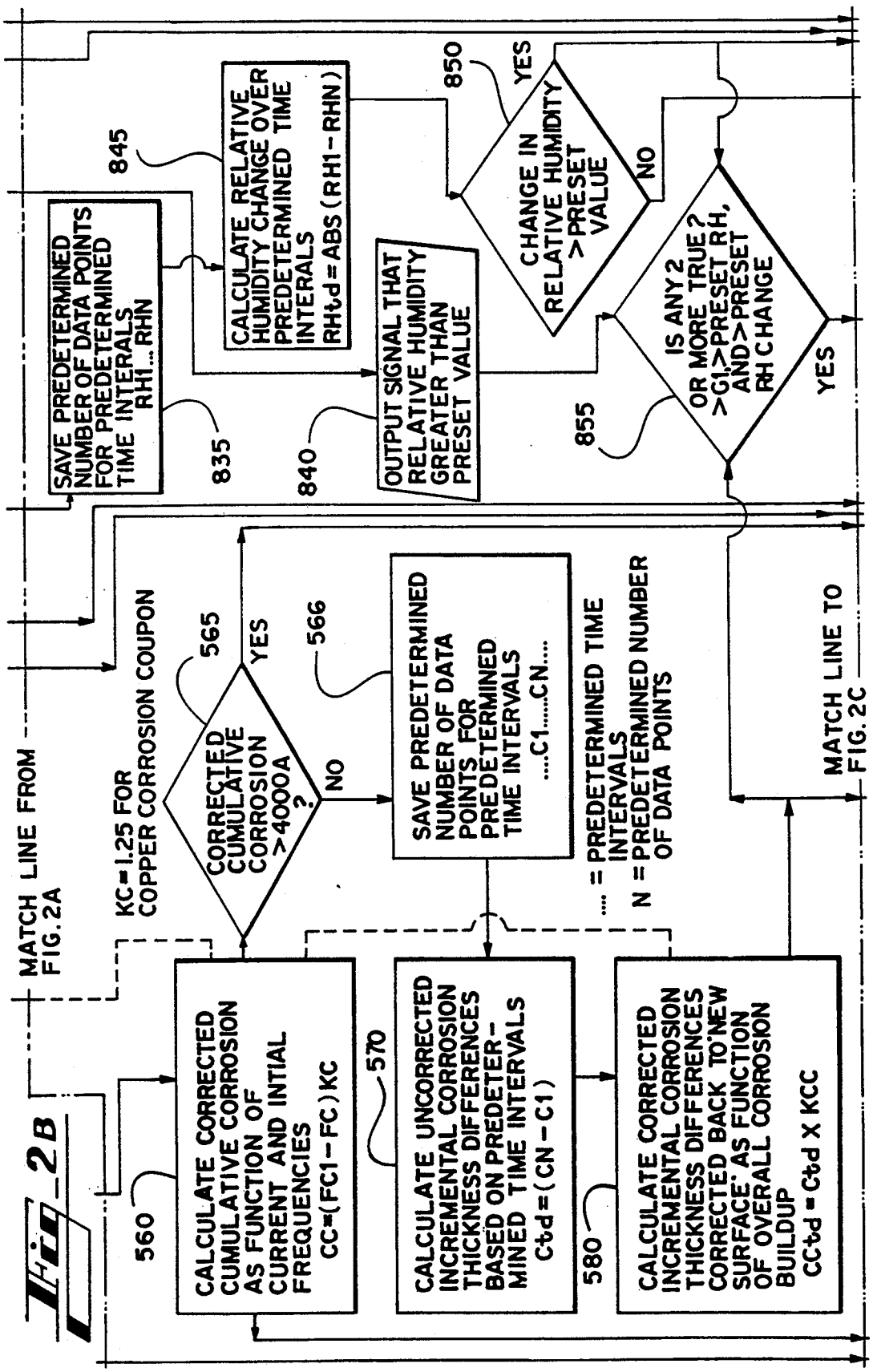

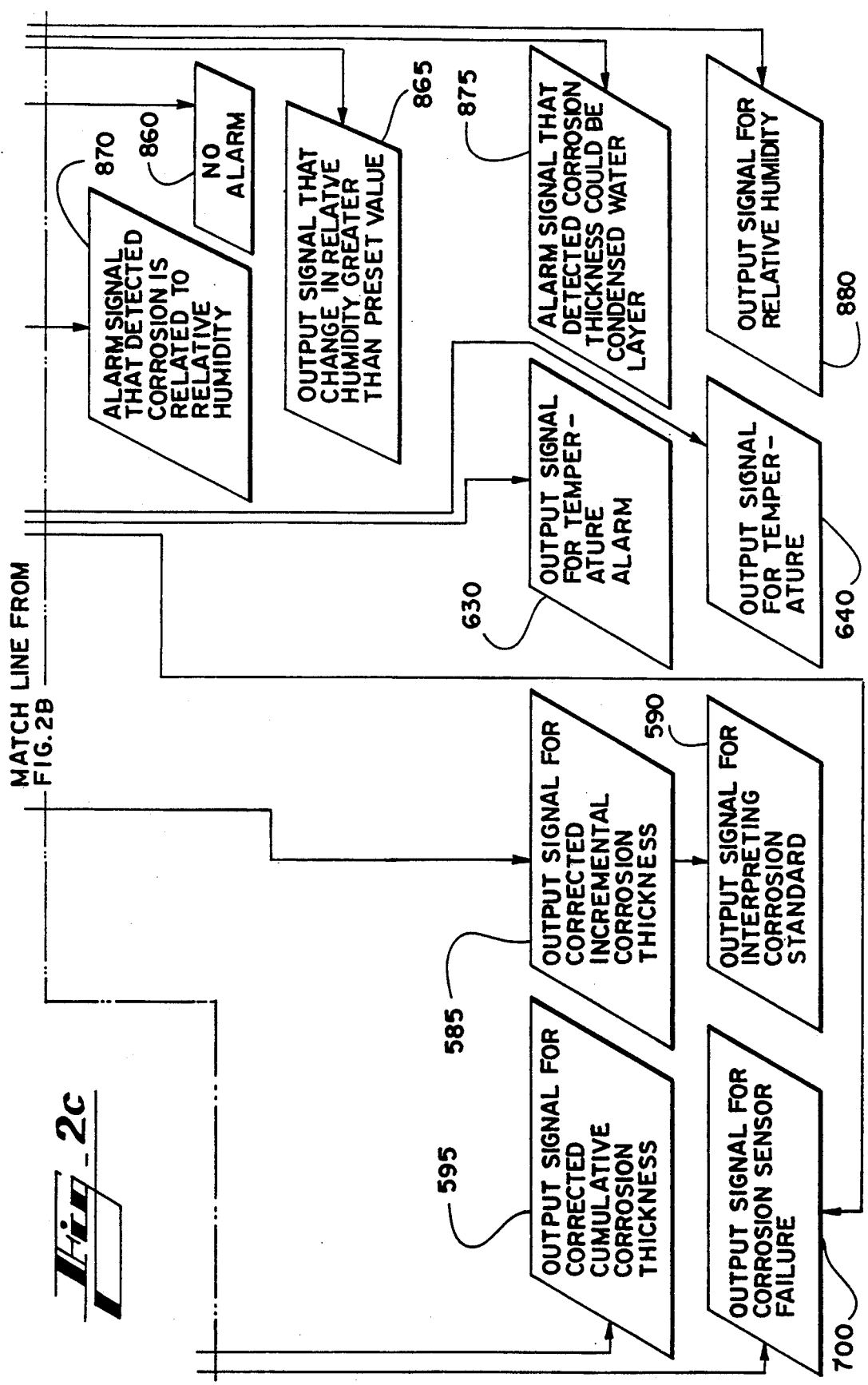
Fig_2c

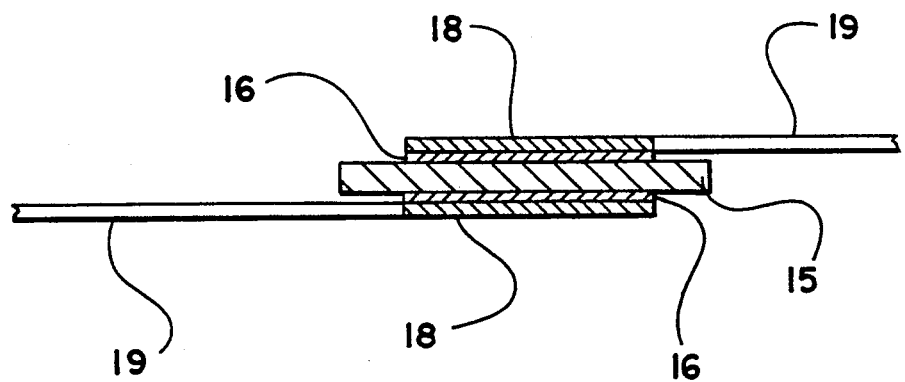
_Fig_3
_Fig_4
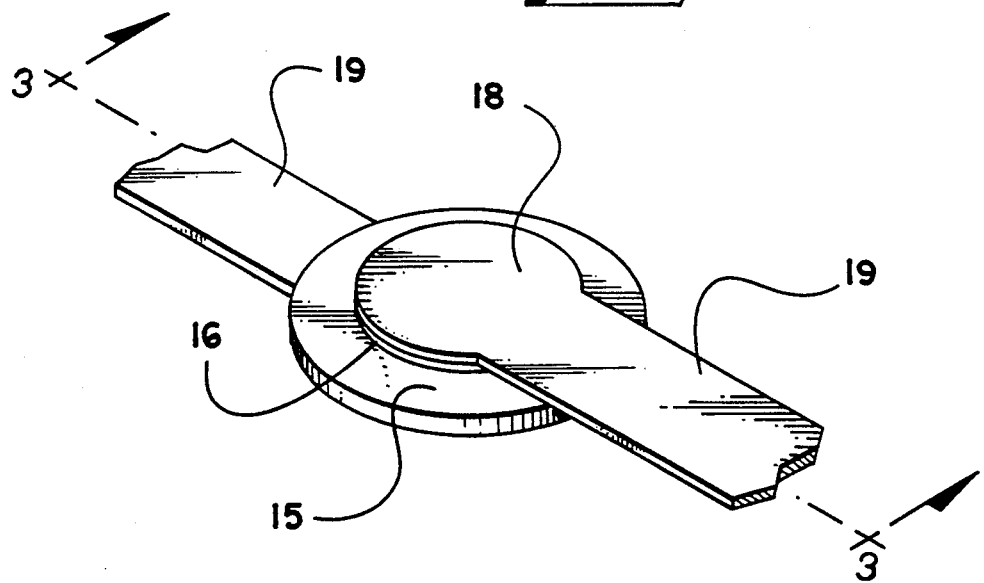

METHOD AND APPARATUS FOR MONITORING CORROSION

CROSS-REFERENCE TO RELATED APPLICATION

This application is a continuation-in-part of Ser. No. 521,079, filed May 8, 1990, now abandoned, and is a continuation of PCT U.S. Ser. No. 91/03097, filed May 6, 1991.

TECHNICAL FIELD

This invention relates generally to a method and apparatus for monitoring corrosion, and particularly to a method of reporting corrosion in terms of an industry-accepted standard of corrosion thickness, taking into consideration variances in atmospheric conditions such as temperature and humidity.

BACKGROUND OF THE INVENTION

Many metal-containing devices and structures must function in corrosive atmospheres which cause them to deteriorate over time. Corrosion may take the form of metal oxides resulting from reaction with oxygen in the air, or may by compounds formed with the effluent of industrial processes, such as hydrogen sulfide.

In the electronics industry, for example, approximately one-third of all warranty repair work is attributable to corrosion. Accordingly, the ability to accurately monitor corrosion and take appropriate measures to deter its spread are of utmost importance to the industry.

The standard method of monitoring corrosion has historically been accomplished using a reactivity monitoring procedure such as the so-called "coupon" method. Under this method, strips of copper are placed in the environment where corrosion is to be monitored. The coupons carry an initial copper oxide corrosion thickness of about 100 Angstroms (Å). After a period of time in the environment, usually around thirty days, the change in thickness of corrosive buildup on the strips, or coupons, is measured using a complex coulometric reduction procedure, well known to those skilled in the art.

Using an accepted standard such as Standard No. ISA-S71.04-1985 set by the Instrument Society of America (ISA) of Research Triangle Park, N.C., this change in thickness is then projected over a chosen period of time. Other organizations, such as Battelle of Columbus, Ohio, have also developed such standards which, like the ISA standard, are based on reactivity monitoring techniques. Given a corrosive buildup after any number of days, the standard may be applied to project the weekly, monthly, or annual buildup of corrosion in the environment. Such information is vital to the electronics industry in determining the reliability and projected lifetime of equipment. It may affect the scope or duration of warranty coverage, particularly in limiting such coverage when the equipment will be used in corrosive environments. The reactivity monitoring method of corrosion monitoring using coupons is discussed in further detail in "Environmental Conditions and Process Measurement and Control Systems: Airborne Contaminants," a 1985 ISA publication; and Krumbein, Newell, and Pascucci, "Monitoring Environmental Tests by Coulometric Reduction of Metallic Control Samples," *Journal of Testing and Evaluation*, Vol. 17, No. 6, Nov. 1989, pp. 357-67, both of which are incorporated herein by reference. Although copper, silver, and nickel are part of the electronic circuitry, copper is the only metal addressed by the ISA standard. Accordingly, there is a need in the art to monitor the corrosion of electronics circuitry containing other corrodible metals, in addition to copper. References to corrodible metals herein include any corrodible metal, and also include such metals coated with gold. Examples of corrodible metals, without limitation thereto, are copper, silver, nickel, and laminates of such metals which may or may not be coated with gold.

One major disadvantage of the coupon method of reactivity monitoring, however, is the destructive nature of the measurement. Once the thickness of corrosion on the coupon has been measured, the coupon must be discarded and, although the measurement may be projected over a desired period of time, further actual corrosion measurements may only be taken with a new coupon. Accordingly, there is a need in the art to provide a non-destructive method for measuring corrosion in terms of recognized reactivity monitoring standards.

One possible solution to this problem is to measure the corrosion buildup in terms of frequency change. Such a solution has been disclosed in the prior art writings of Lu and Czanderna, APPLICATIONS OF PIEZOELECTRIC QUARTZ CRYSTAL MICROBALANCES (Elsevier, 1984), pages 203-05; and Lee, Siegmann, and Eldridge, "A Comparison of the Mass and Resistance Change Techniques for Investigating Thin Film Corrosion Kinetics," 124 *Journal of the Electrochemical Society* (May 1977, pages 1744-47), which are both incorporated herein by reference. The use of a piezoelectric crystal to analyze corrosion is also generally disclosed in U.S. Pat. No. 4,783,987, to Hager et al., also incorporated herein by reference. These references teach the use of a quartz crystal microbalance (QCM) which is attached to an oscillator, from which the frequency of vibration of the QCM is measured. As the metal layered on the quartz crystal corrodes over time, the frequency of the QCM changes, thus providing an indication of corrosion in terms of frequency change.

Measuring the change in frequency of the QCM enables one to conduct real-time measurements of corrosion. Unlike the reactivity monitoring coupon method, which requires a new, unblemished coupon each time the thickness of corrosion is measured, frequency measurements may be repeated time and time again as the corrosion continues to accumulate without destroying the QCM. However, an indication of frequency change does not allow comparison with specifications stated in terms of an accepted industry standard of corrosion measurement which is stated in terms of thickness.

It should be noted that a reactivity monitoring coupon prepared according to the ISA standard has a surface quite different from that of a coated crystal. The ISA standard requires that the coupon, a metal strip, be sanded or abraded. Thus, the coupon presents a rough surface to the corrosive atmosphere. In contrast, the metal layer on a coated crystal is vacuum deposited to form a shiny, smooth surface. Corrosion forms differently on such different surfaces. Therefore, finding a correlation between corrosion on a coated crystal detected by means of a change in the frequency of vibration of the crystal, and the corrosion that would have occurred under the same conditions on a new, unblemished coupon prepared according to a standardized reactivity monitoring procedure, is not a simple or obvious matter.

U.S. Pat. No. 3,253,219, to Littler, describes the use of a piezoelectric crystal to measure the decrease in thickness over time of a test specimen, such as a vinyl acetate resin, which is adhered to the crystal. As the thickness of the specimen decreases, the frequency of vibration of the crystal increases. When a crystal with a 3.5 MHz oscillating frequency is utilized, a decrease in thickness of 1 Å is said to be equivalent to an increase in frequency of 1 Hz. Littler, however, does not address the corrosion of metals, which are the subject of the electronic industry's concerns. Our tests have shown that Littler's teaching regarding the thickness change of eroding plastics does not hold true for corroding metals laminated on the vibrating crystals we have tested. Thus, there has been a need in the art for a corrosion monitor using a piezoelectric crystal that can report corrosion measurements in terms of an accepted reactivity monitoring standard. Furthermore, Littler does not suggest or disclose any means for monitoring, generating, or displaying the thickness of corrosion. Importantly, Littler does not address the impact of atmospheric factors, such as air temperature or relative humidity, on the ability to accurately monitor the buildup of corrosion.

U.S. Pat. No. 4,869,874, to Falat, which is incorporated herein by reference, describes a device which measures corrosion, taking into account atmospheric conditions such as temperature, pressure, and humidity by comparing existing conditions to present limits. However, in order to achieve accurate, useful results, Falat requires that the monitoring occur over an extended designated period of time, usually on the order of about six months. There is therefore a need in the art to provide a corrosion monitor that takes atmospheric conditions, such as temperature and humidity, into consideration and provides accurate, useful data on an as-needed basis, as frequently as daily.

SUMMARY OF THE INVENTION

The present invention fulfills the needs in the prior art. Broadly described, the present invention provides a method and apparatus for using a piezoelectric crystal to monitor and report corrosion in terms recognized as conforming to an industry standard.

Generally described, the present invention provides a method of and system for monitoring corrosion in a corrosive atmosphere, comprising and carrying out the steps of exciting in the atmosphere a crystal, coated with a corrodible metallic substance and having a known vibration frequency; measuring the change in the frequency of vibration resulting from corrosion of the corrodible substance during each of a plurality of intervals of time, including an initial interval and at least one subsequent measurement interval; and generating a thickness signal representing the thickness of corrosion that would have accumulated during said measurement interval utilizing a standardized reactivity monitoring procedure.

In a preferred embodiment, the invention also includes correcting the measured frequency change during each measurement interval to account for any deviation in the temperature in the atmosphere from a preset standard temperature. The thickness signal thus preferably represents the thickness of corrosion in accordance with ISA or other reporting standards, based upon the temperature-corrected frequency change. Optionally, an intermediate thickness signal can be generated representing the thickness of corrosion during the measurement interval prior to conversion to a value representing the thickness of corrosion that would have accumulated during said measurement interval utilizing a standardized reactivity monitoring procedure.

Thus, the intermediate thickness signal representing corrosion is preferably generated by multiplying the temperature-corrected frequency change during the measurement interval by a predetermined factor necessary to convert the frequency change to a thickness value. Although the corrosion on the coated crystal can be determined in such a manner for any desired interval, the correlation to a standardized reactivity monitoring standard is not complete until the intermediate corrosion thickness value for any given interval is further converted to represent the corrosion thickness that would have resulted if, at the beginning of the interval, a new, unblemished reactivity monitoring coupon prepared according to the standard had been used to monitor corrosion during the interval.

The present invention also preferably includes a humidity sensor, which serves as the impetus for providing an alarm to the user if the relative humidity is above a preset limit, or if the relative humidity changes during an interval by more than a preset limit.

The present invention may also provide for displaying the thickness signal, the temperature, and the relative humidity. Such outputs may also be directed to other devices such as digital storage or graphical recorders, and they also may be used to trigger alarms to the user.

In the preferred embodiment of the present invention, a piezoelectric crystal, such as a 6 Mhz "AT cut" quartz crystal in a mounting such as the "Holder Series W-8" manufactured by McCoy Electronics Company of Mt. Holly Springs, Pa., is coated with a corrodible metal as defined above. The coated crystal is mounted on a three-prong stand, dried in an oven, and cleaned. It has been found that cleaning with a chlorinated flux solution followed by rinsing in distilled water and boiling in alcohol removes any unwanted coatings that may be deposited in the process of curing the coated crystal in the holder. A suitable flux is Flux Solution 709, made by Alpha Metals of Atlanta, Ga. Preferably, the coated crystal is surrounded by an inert gas and sealed from the ambient air until the monitor is ready for use. The QCM is then placed in a corrosive atmosphere and can be connected to an oscillator before or after placement in the corrosive atmosphere. As the corrodible metal corrodes, the frequency of vibration of the QCM decreases. The frequency reading is then converted, using factors determined in a manner described below, to a thickness reading corresponding to a selected corrosion thickness standard.

A corrosion monitor according to the present invention finds application in such environments as industrial process measurement and control rooms, motor control centers, electrical rooms, semiconductor clean rooms, electronic fabrication sites, commercial data centers, museums, libraries, and archival storage rooms. It is also useful for checking the exhaustion level of filtration media being used to protect the environment of such spaces.

Accordingly, it is an object of the present invention to provide an apparatus for using a coated piezoelectric crystal to monitor and report corrosion in terms recognized as conforming to an industry standard reactivity monitoring procedure.

It is another object of the present invention to provide a method for using a coated piezoelectric crystal to monitor and report corrosion in terms recognized as conforming to such an industry standard.

It is another object of the present invention to provide a method and apparatus for converting frequency measurements obtained from a sample of corroding metal to thickness values which conform to such an industry standard for measuring corrosion.

It is a further object of the present invention to provide a method and apparatus for correcting measured changes in frequency of a vibrating crystal coated with a corroding metal in order to account for deviations in temperature from a certain predetermined standard temperature.

It is another object of the present invention to provide a method and apparatus for generating a signal corresponding to the change in corrosion thickness during any desired interval of time, and also for converting the signal so as to relate it to an industry reactivity monitoring standard which requires that each interval begin with a new, unblemished prepared specimen.

It is another object of the present invention to provide a method and apparatus for determining whether certain atmospheric conditions related to the relative humidity are contributing to corrosion in a corrosive atmosphere and, if so, generating an alarm signal informing users of the present invention of such conditions.

These and other objects, features, and advantages of the present invention may be more clearly understood and appreciated from a review of the following detailed description of the disclosed embodiment and by reference to the appended drawings and claims.

BRIEF DESCRIPTION OF THE DRAWING FIGURES

FIGS. 2A to 2C show a flow chart representing the corrosion monitoring method embodied by the present invention.

FIG. 3 is a cross-sectional view of a plated quartz crystal and the various layers of metallic substances coated thereon, utilized in the preferred embodiment of the present invention.

FIG. 4 is perspective view of the quartz crystal shown in FIG. 3.

DETAILED DESCRIPTION OF THE PREFERRED EMBODIMENT

Figure 1:
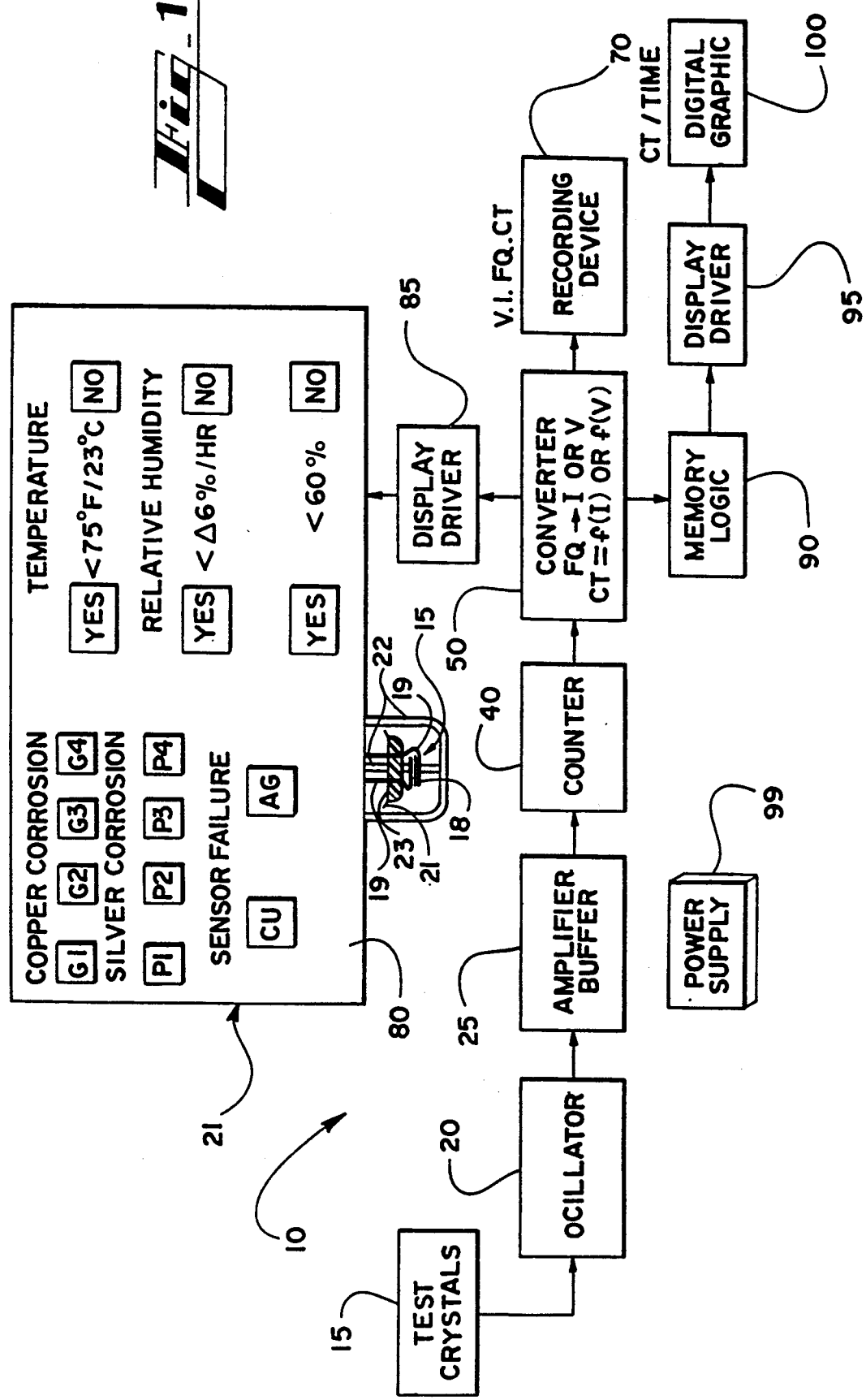
FIG. 1 is a schematic diagram of a corrosion monitor embodying the present invention.

Referring now to the drawings, in which like numerals indicate like elements throughout the several views, FIG. 1 is a schematic representation of a preferred corrosion monitor 10 embodying the present invention. One or more coated quartz crystals 15 are attached to an oscillator 20, which drives the vibration of the coated crystal 15 and outputs signal pulses corresponding to vibrations of the coated crystal. The oscillator output is provided to a counter 40 via a bridge 25 which includes an amplifier and a buffer. The buffer prevents the oscillator from being affected by the load of the counter 40, and the amplifier amplifies the digital output of the oscillator 20 to provide suitable input for the counter 40. The counter 40 counts the pulses from the oscillator to determine the frequency of the coated crystal as the frequency changes resulting from the corrosion of the metallic substance layered upon the coated crystal 15.

FIGS. 3 and 4 illustrate the preferred embodiment of the coated quartz crystal 15. An approximately 30 Å thick layer of chromium 16 is bonded or deposited onto both the top and bottom surfaces of the crystal 15, and a layer of a corrodible metallic substance 18 is then bonded or deposited onto each of the layers of chromium. The thickness of the metallic substance 18 depends upon the type of substance employed, as the examples discussed below illustrate. The chromium 16 serves to bond the corrodible metal 18 to the crystal 15. The oscillator 20, which is illustrated in the schematic drawing in FIG. 1, is attached to the layers of corrodible metal substance 18 by leads 19. The construction, mounting, cleaning and driving of the crystal 15 utilize techniques well known in the QCM art. A preferred example is described above.

A preferred crystal mounting arrangement is shown in FIG. 1. One or more coated crystals 15 of FIGS. 3 and 4 are supported below a case 21. The leads 19 pass upwardly through openings in a tin plated steel dish 21 into the case where they are connected to electronic circuitry. The leads 19 are potted to the dish with epoxy 23. The coated surface of the crystal 15 is preferably oriented to face downwardly to avoid excess accumulation of dust. A protective cage 22 may be placed around the crystal assembly to prevent accidental contact with the crystal or its coated surface. However, the cage 22 should not appreciably restrict the flow of ambient air past the coated crystal. Multiple coated crystals may be used with one monitor 10, and may carry different corrodible metals 18, as defined above.

The frequency of each coated crystal 15, which decreases as the metallic surface layered upon the crystal corrodes, is output to the counter 40. The counter 40 also includes conventional circuit elements (not shown) for zeroing the counter output at the original frequency of the coated crystal prior to exposure to the corrosive atmosphere. Therefore, the output from the counter 40 represents the change in frequency of the coated crystal caused by corrosion. The temperature in the corrosive atmosphere is sensed by the temperature sensor 55, and the relative humidity of the corrosive atmosphere is also sensed, by a humidity sensor 58. The temperature sensor is preferably of a conventional design such as a National Semiconductor Corp. Model LM35. The humidity sensor is preferably of a conventional design such as a Minicap 2 model, manufactured by Panametrics. The counter 40, temperature sensor 55, and the humidity sensor 58 provide output signals to a programmable converter circuit 50. The converter 50 is preferably a programmable 80C31 microprocessor operating at 8.3886 MHz.

A number of conversion steps occur in the converter circuit 50 as further detailed in FIG. 2, and described in detail below. The frequency input from the counter 40 is corrected to allow for any deviations from a predetermined standard temperature. Also in the converter 50, the frequency is converted to either an analog voltage or an analog current signal, and the voltage or current signal representing the frequency change is then converted to provide a measurement of corrosion thickness which conforms with the ISA standard of corrosion thickness, in Angstroms, corresponding to starting with a clean corrodible surface. This is done by applying to the frequency signal appropriate factors, depending upon the type of corrodible metal on the crystal 15, the nature of the crystal, and the temperature. Determination of the factors used for these conversions is described below. In addition, if the relative humidity is above a specific predetermined limit, or if the relative humidity has changed by more than a predetermined variation, an appropriate signal will be generated.

Once the final corrosion thickness value is obtained, this value is then preferably output to three separate storage and display media of conventional construction, driven by analog input. The corrosion thickness value is output from the converter 50 to a recording device 70, such as a chart recorder, along with the frequency change signal and voltage/current signals corresponding to the frequency change. These three values may also be displayed on a LED or LCD display 80, after being prepared for the device 80 by a conventional display driver 85. The output signals from the temperature and humidity sensors, which are in the form of frequencies, may also be converted to temperature and humidity values by the converter, and displayed by the display 80. Finally, the corrosion thickness value in Å may also be stored in the memory of a conventional microprocessor 90, where it is analyzed and prepared for digital graphic display. The corrosion thickness may then be displayed in graphic form on a digital graphic display monitor 100 driven by a display driver 95 in terms of corrosion thickness over a specific period of time. All values determined by the system may be sent to remote computers via an RS485 serial output port (not shown).

A power supply 99, with suitable transformers as required, is connected to the various components by lines (not shown). It will be understood that the specifications of the electronics and circuitry illustrated in FIG. 1 are of a type that is generally known to those who are skilled in the art.

Turning now to FIG. 2, the logic flow of the operation of the corrosion monitoring device 10 may be seen. FIG. 2 is a flow chart for the functions carried out by the converter 50, which may be programmed to perform such functions by one of ordinary skill in the programming art. As discussed above, the corrosion monitor includes three primary sensors, a corrosion sensor 15, a temperature sensor 55, and a relative humidity sensor 58. The main features of the corrosion sensor 15 are further detailed in FIGS. 3 and 4. Typical operation of the corrosion monitoring device is as follows.

Monitoring of corrosion with the device 10 occurs at a series of intervals of time. At the beginning of each interval, the uncorrected vibration frequency FU is read at block 520 of FIG. 2 from the output of the counter 40. The frequency FU is then monitored every few seconds at block 530 using conventional quartz crystal monitoring techniques. If the frequency FU is unstable or has a value that is too high or too low according to preset parameters, then the device generates an output signal for corrosion sensor failure, at block 700. If the frequency FU remains stable and within an acceptable range, the converter then corrects the frequency FU for any deviation in temperature from a standard, predetermined temperature, at 540.

The step of correcting the frequency as a function of temperature, at 540, brings the temperature sensor 58 into play. The temperature sensor 58 provides a signal which is converted into a temperature reading, at block 610. The temperature reading is used for two purposes. First, the temperature reading is compared to a predetermined limit, at block 620, and is output as previously described, at block 640. The limit value is preferably selected to be within the ISA standard for corrosion measurements: 70°-75° F. If the temperature reading is above the limit value, an output signal is generated indicating a temperature alarm, at block 630. The temperature reading is also used to correct the frequency at block 540, giving a temperature-corrected frequency FC. The temperature-corrected frequency FC is determined by applying a correction formula to the uncorrected frequency. The applicable formula varies depending upon the type and size of corrodible coated crystal employed, and this formula can be determined by exposing a coated crystal in a controlled temperature environment and recording the variation in frequency with changes in temperature.

EXAMPLE 1

A 6 MHz, AT cut quartz crystal coated with copper and connected to oscillation and frequency detection circuits as described herein is placed in a test atmosphere which also contains an NBS traceable thermometer. Over a one hour period the temperature in the test atmosphere is changed from 35 to 90 degrees F., and the changing temperature is compared to the change in frequency of vibration of the quartz crystal. The correction formula for this coated crystal based on the empirical data is determined to be:

$$FTC = -(2/5)(T - 70° F.)$$

where FTC is the frequency correction at temperature T. The temperature-corrected frequency FC is obtained by subtracting FTC from FU.

After the temperature-corrected frequency FC is obtained, the device inquires at block 550 as to whether the particular temperature-corrected frequency FC being evaluated is the initial temperature-corrected frequency FC, namely whether the measurement is at the beginning of the first interval of the monitoring process. If so, the initial temperature-corrected frequency FC is saved, at block 555, as the initial temperature-corrected frequency $FC_i$.

For each interval, the corrected cumulative corrosive buildup CC, represented in the ISA standard of thickness, is calculated, at block 560. The cumulative buildup is determined by subtracting the temperature-corrected frequency FC for the end of the particular interval being monitored from the initial temperature-corrected frequency $FC_i$ to obtain a cumulative corrected frequency change. Because the frequency reading decreases as the corrosive buildup on the coated crystal increases, this will be a positive value. The result is then multiplied by a conversion factor KC, which, like the temperature correction determination, varies depending upon the crystal type and size. The result is cumulative corrosion thickness in Å.

The conversion factor KC is may be determined for a coated crystal by placing the coated crystal in a test duct along with ISA reactivity monitoring coupons in a corrosive gas, and comparing the corrosion of the coupons to the change in frequency of the crystal.

EXAMPLE 2

Two 6 MHz, AT cut quartz crystals, one coated with copper and the other with silver, are connected to oscillation and frequency detection circuits as described herein and placed in a test duct containing a flow of corrosive gas capable of producing about 250 to 300 Å of corrosion per day with no temperature or relative humidity control. Fifteen copper and silver reactivity coupons conforming to ISA specifications are also placed in the duct. Every day one copper and one silver coupon are removed for cathodic/electrolytic reduction to determine the amount of corrosion according to the ISA standard method. The results are compared to the frequency change of the coated quartz crystals over the same period to determine a relationship between the frequency change and the corrosivity of the atmosphere measured according to the ISA standard method. Similar tests have shown that multiplying the frequency change by a factor KC of about 1.25 for this type of coated crystal gives the corresponding ISA corrosion thickness in Å for both copper and silver coatings.

Given the correction factor KC, the corrected cumulative corrosion CC may be determined at block 560 using the following formula:

$$CC = (FC_i - FC)KC$$

After determining the corrected cumulative corrosive buildup CC, it is output for storage or display at block 595. The value of CC is also compared to 4000 Å, at block 565. A buildup of corrosion beyond this level renders the coated crystal unreliable. If the corrected cumulative corrosive buildup CC is greater than 4000 Å, then an output signal for corrosion sensor failure is generated, at block 700. If the corrected cumulative corrosive buildup CC is not greater than 4000 Å, then the corrosive buildup is within acceptable parameters and the monitoring process continues. The corrected cumulative corrosive buildup CC is saved for each interval being monitored, at block 566. For a 24 hour interval, 96 data points will be saved, one every 15 minutes. Conventional smoothing techniques may be carried out by the converter 50 in acquiring data points. The uncorrected incremental corrosion thickness differences $C_{td}$ are calculated for each particular 24 hour interval, at block 570, by subtracting the value of CC at the end of any 24 hour interval, represented as CN, from the value of CC at the beginning of the same 24 hour interval, represented as C1. The 24 hour calculated values are updated every 15 minutes as a new data point is acquired and saved.

The next step in the process is to relate the uncorrected incremental corrosion thickness difference $C_{td}$, for any particular interval of time, back to an industry standard, such as the ISA standard, which requires beginning each monitoring period with a prepared reactivity monitoring coupon which has not been exposed to the corrosive atmosphere. Calculation of the "related back" corrosion thickness $CC_{td}$ is accomplished at block 580 by multiplying the uncorrected incremental corrosion thickness differences $C_{td}$ by a corrective value KCC. Output of the signal $CC_{td}$ for display or storage in numerical form occurs at block 585, while output in the form of a signal that represents the corrected incremental corrosion level in terms of the ISA standard notations of G1, G2, G3, or GX occurs at block 590. In block 590, the converter determines in which ISA range the numerical value for corrected incremental corrosion falls. The ISA standard corrosion categories of G1, G2, G3, and GX are well known in this industry. However, since the ISA values for these ranges are based on one month's corrosion beginning with a prepared reactivity monitoring coupon which in fact has an initial corrosion layer of about 100 Å, the converter uses the following approximate values for the coated quartz crystal over a period of one day:

|  | ISA - One Month | Coated Crystal - One Day |
|---|---|---|
| G1 | <300Å | <6.7Å |
| G2 | <1000Å | <30Å |
| G3 | <2000Å | <63.3Å |
| GX | >2000Å | >63.3Å |

Determination of the particular value for KCC is again dependent upon the type and size of the coated crystal employed, and also changes as corrosion builds on the coated crystal. However, the value for KCC can be determined empirically by comparing the relationship between the test results obtained using the ISA reactivity monitoring coupon method and those obtained by using the corrosion monitoring device of the present invention.

EXAMPLE 3

Three 6 MHz, AT cut copper coated crystals connected to oscillation and frequency detection circuits as described herein are placed with three ISA reactivity monitoring coupons in an isolated atmospherically controlled chamber having a constant relative humidity (50%) and temperature (22° C.). Known concentrations of corrosive gases capable of producing about 400 Å of corrosion per day are used to expose the coupons and coated crystals. The coated crystals remain in the chamber, and each day the change in the frequency of the coated crystals is determined. Each day, however, the coupons are removed and replaced with three new prepared coupons. The removed coupons are then tested for corrosive buildup using known ISA approved techniques, so that each day the frequency change of the coated crystals can be compared to the corrosive buildup on the prepared coupons. With this 6 MHz coated crystal, the formula for determining KCC is found to be:

$$KCC = 2 - (1 - CC/4000)$$

where CC is the corrected cumulative corrosive buildup for the end of a particular time interval.

Thus, the process of the present invention allows for monitoring corrosion with a vibrating coated crystal, for any given interval, in terms of thickness of corrosion corresponding to the use of a prepared ISA reactivity monitoring coupon at the outset of the interval. The longevity of the coated crystal is a great advantage as compared to the ISA coupon, which must be destroyed to measure corrosion. Compensation for atmospheric conditions, as described herein, is another advantage of the present invention not contemplated in the prior art.

In the foregoing description, references to ISA standards relate to corrosion of copper, and this ISA standard for copper is used as a particular non-limiting example. It should be understood as noted above that different standards for copper and for other metals can be identified and programmed into the converter 50.

Throughout the monitoring process, the relative humidity sensor 58 is employed. The humidity sensor 58 provides a signal which is converted into a reading of the relative humidity, at block 810, and output for display or storage at block 880. The relative humidity reading is provided to help users of the corrosion monitoring device to determine whether humidity is a cause of corrosive buildup in the atmosphere. The first use of the relative humidity reading is at block 820, where the relative humidity reading is compared to 100%, a value corresponding to a condensed water layer. If the relative humidity reading is 100%, an alarm signal is generated, at block 875. If the relative humidity reading is not 100%, then a signal indicating no alarm is generated, at block 825, and the relative humidity reading is then compared to a predetermined maximum value, at block 830, which may be for example, 60%. If the relative humidity reading is greater than the predetermined maximum value, then an output signal to that effect is generated, at block 840. If the relative humidity reading is not greater than the predetermined maximum value, then the relative humidity readings at each 15 minute data acquisition interval over a 24 hour period are saved as data points, at block 835.

The change in relative humidity $RH_{td}$ for a selected time interval is then calculated, at block 845, by comparing the relative humidity at the end of the interval, $RH_n$, to the relative humidity at the beginning the particular interval, $RH_1$. If the change in relative humidity $RH_{td}$ for a particular time interval is greater than a particular preset value for humidity change, such as a 6% change in one hour, as determined at block 850, then an appropriate output signal is generated, at block 865. If the change in relative humidity $RH_{td}$ for a particular time interval is not greater than the preset value for humidity change, then a signal indicating no alarm is generated, at block 860.

The use of the humidity sensor 58 is tied in to data from the corrosion and temperature sensors 15, 55 at block 855, which receives the signal $CC_{td}$ from block 580, the relative humidity value, and the output from block 850. Three questions are posed at block 855, namely, whether the relative humidity reading is greater than the preset maximum value of block 830, whether the change in relative humidity reading from one interval to the next is greater than the preset maximum change of block 850, and whether the corrected incremental corrosion thickness $CC_{td}$ is greater than the limit represented by the "G1" notation under the ISA standards. If any two of the questions are answered affirmatively, an alarm signal is generated, at block 870, indicating that any corrosion is likely related to the humidity.

The display device 80 may display numerical values for the various data sensed or calculated by the converter 50, or may provide indicator lights as shown in FIG. 1. As shown, a row of LED's is provided for indicating the copper corrosion level, using the ISA notation G1, G2, G3, or GX. A similar row of LED's is provided for silver corrosion levels selected by the manufacturer. The output for these LED's is triggered in the logic at block 590 of FIG. 2. Also provided are two LED's for indicating failure of the copper and the silver coated crystals, activated at block 700. Two further LED's indicate whether or not the temperature is greater or lower than the threshold of block 620, and are activated at blocks 625 and 630. Another pair of LED's indicate whether or not the relative humidity has changed more than a preset amount in the last time interval (blocks 850, 860 and 865), and a final pair of LED's indicate whether or not the relative humidity has exceeded the preset maximum value (blocks 830 and 840).

Figure 5:
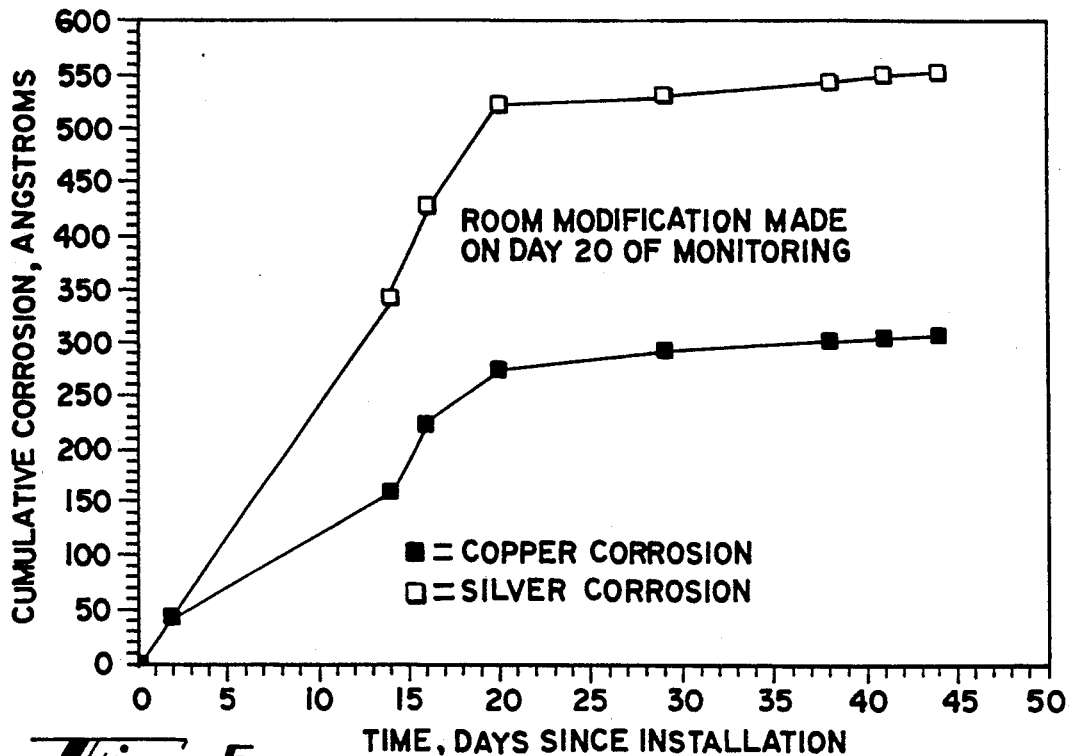
FIG. 5 is a graphical representation of the performance of the preferred embodiment of the present invention with respect to cumulative corrosion data.
Figure 6:
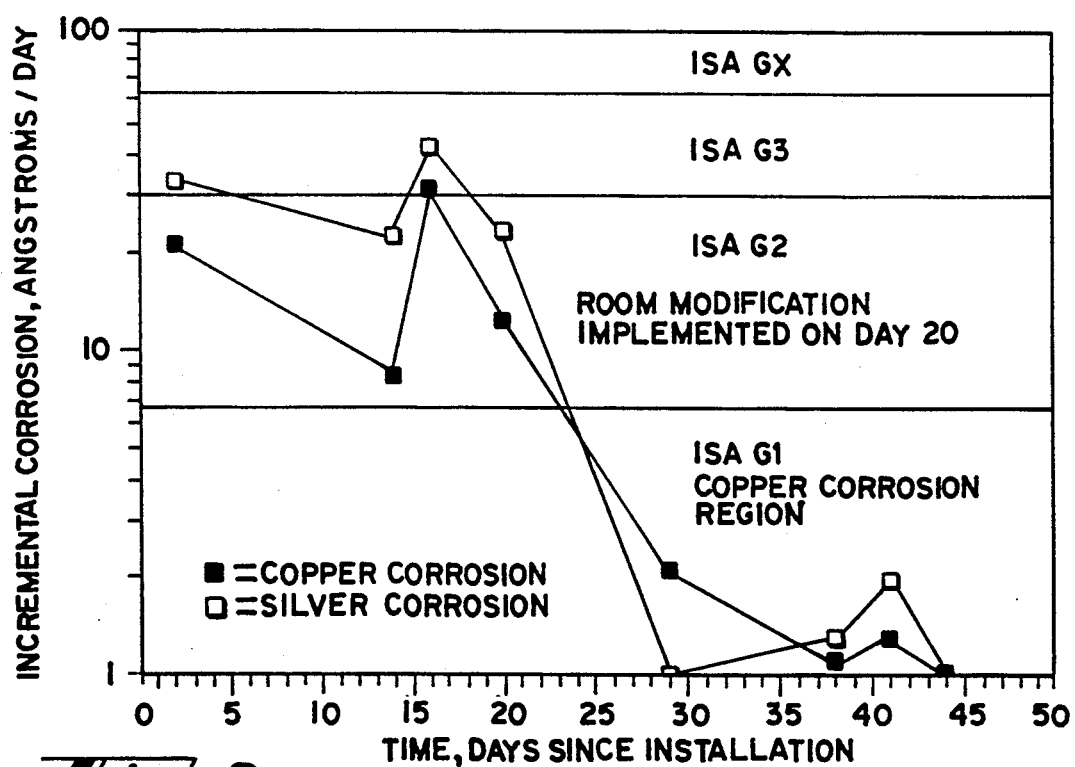
FIG. 6 is a graphical representation of the performance of the preferred embodiment of the present invention with respect to incremental corrosion data, with a particular interval of one day.

Turning now to FIGS. 5 and 6, the performance advantages of the preferred embodiment of the present invention are illustrated. FIG. 5 is a graphical representation of the performance of the present invention, reported in terms of corrected cumulative corrosive buildup CC, which is fully detailed in the discussion of FIG. 2. As illustrated in FIG. 5, the corrected cumulative corrosive buildup CC may be reported for any given day throughout the testing period. The measurement of the corrosive buildup on the coated crystal on any given day does not in any way impede the ability to use the same coated crystal to accurately measure corrosion at a later time. Similarly, FIG. 6 is a graphical representation of the corrected, or "related back," incremental corrosion thickness $CC_{td}$, also detailed in the discussion of FIG. 2. The graph illustrates the amount of corrosion in terms of the four ISA corrosion categories, described hereinabove. As with the cumulative corrosive buildup CC, the corrected, or "related back," incremental corrosion thickness $CC_{td}$ may be reported for any given increment without necessitating the destruction of the test coated crystal. As is also clearly evident from the information depicted in FIGS. 5 and 6, the corrosion monitoring method of the present invention allows for the rapid and efficient correction of corrosion-causing conditions by giving an accurate indication of corrosion rate much sooner than prior methods. In both FIGS. 5 and 6, it is clear that when the room modifications were made, at day 20, the corrosive buildup substantially decreased, to the point that the curve in FIG. 5 is nearly a straight line and the data points in FIG. 6 all fall within the G1, or least corrosive, category under the ISA standard. In contrast, the Falat reference suggest that monitoring will take on the order of six months, and the ISA standard is based on at least 30 days of exposure of a test coupon, followed by a time-consuming chemical analysis of the coupon. Additionally, by plotting corrosion on an interval basis, such as is illustrated in FIG. 6, corrosion-causing events can be more readily tracked.

Accordingly, it will be understood that the preferred embodiment of the present invention has been disclosed by way of example and that other modifications and alterations may occur to those skilled in the art without departing from the scope and spirit of the appended claims.

What is claimed is:

1. A method of monitoring corrosion in a corrosive atmosphere, comprising the steps of:
    exciting in the atmosphere a crystal, coated with a corrodible metallic substance and having a characteristic vibration frequency;
    obtaining an initial frequency measurement of said crystal at the time of initial exposure of said crystal to the atmosphere;
    periodically obtaining subsequent frequency measurements of said crystal at times after said initial frequency measurement;
    determining and monitoring the cumulative corrosion thickness built up on said crystal from the time of initial exposure to each of the times of said periodic subsequent frequency measurements;

defining a measurement interval beginning at the time of one of said subsequent frequency measurements and ending at the time of another of said subsequent frequency measurements; and converting the frequency change from the beginning to the end of said measurement interval to a corrosion thickness signal corrected by a corrective value dependent on the cumulative corrosion built up on said crystal;

said corrected corrosion thickness signal representing the corrosion thickness that would have resulted if, at the beginning of said measurement interval, a new, unexposed reactivity monitoring coupon prepared according to a reactivity monitoring standard had been used to monitor corrosion during said measurement interval, expressed in accordance with said standard.

2. The method of claim 1, wherein said coated crystal initially vibrates at about 6 MHz, and wherein said corrective value is about:

$$2-(1-(CC/4000))$$

where CC is said cumulative corrosion thickness value at the end of said measurement interval.

3. The method of any of claim 1, further comprising the steps of:

monitoring the relative humidity in said corrosive atmosphere; and providing a warning signal indicating that corrosion in said atmosphere is related to humidity whenever said relative humidity exceeds a predetermined level or rises at greater than a predetermined rate, at the same time as said corrosion thickness signal for one of said measurement intervals exceeds a predetermined thickness.

4. The method of claim 1, wherein said reactivity monitoring standard follows substantially an ISA coupon procedure for monitoring corrosion.

5. The method of claim 1, further comprising the step of correcting said initial and subsequent frequency measurements to account for surrounding temperature variations.

6. The method of claim 5, wherein said step of converting the frequency change from the beginning to the end of said measurement interval to a corrosion thickness signal comprises generating an uncorrected incremental thickness signal prior to applying said corrective value, said incremental thickness signal being obtained by multiplying said temperature-corrected frequency measurements at the beginning and end of said measurement interval by a thickness conversion factor to obtain cumulative corrosion thickness values for the beginning and end of said measurement interval, and subtracting said cumulative corrosion thickness values to obtain said incremental thickness signal.

7. The method of claim 1, wherein said corrective value is determined by comparing frequency changes of said coated crystal with corrosion accumulated on reactivity monitoring coupons placed in a common test atmosphere.

8. The method of claim 7, further comprising the step of storing said corrected corrosion thickness signal.

9. The method of claim 8, further comprising the step of displaying said corrected corrosion thickness signal.

10. The method of claim 9, further comprising the steps of measuring and displaying an indicia of the temperature condition at which said frequency measurements are made.

11. The method of claim 10, wherein said corrodible substance is a metal selected from the group consisting of copper, silver, and nickel.

12. An apparatus for monitoring corrosion in a corrosive atmosphere, comprising:

means for exciting in the atmosphere a crystal, coated with a corrodible metallic substance and having a known vibration frequency;

frequency measuring means for obtaining an initial frequency measurement of said crystal at the time of initial exposure of said crystal to the atmosphere, and for periodically obtaining subsequent frequency measurements of said crystal at times after said initial frequency measurement;

converter means for:

determining and monitoring the cumulative corrosion thickness built up on said crystal from the time of initial exposure to each of the times of said periodic subsequent frequency measurements;

defining a measurement interval beginning at the time of one of said subsequent frequency measurements and ending at the time of another of said subsequent frequency measurements; and converting the frequency change from the beginning to the end of said measurement interval to a corrosion thickness signal corrected by a corrective value dependent on the cumulative corrosion built up on said crystal;

said corrected corrosion thickness signal representing the corrosion thickness that would have resulted if, at the beginning of said measurement interval, a new, unexposed reactivity monitoring coupon prepared according to a reactivity monitoring standard had been used to monitor corrosion during said measurement interval, expressed in accordance with said standard.

13. The apparatus of claim 12, wherein said coated crystal initially vibrates at about 6 MHz, and wherein said corrective value is about:

$$2-(1-(CC/4000))$$

where CC is said cumulative corrosion thickness value at the end of said measurement interval.

14. The apparatus of claim 12, further comprising a temperature sensor, and wherein said converter means includes means for correcting said initial and subsequent frequency measurements to account for surrounding temperature variations.

15. The apparatus of claim 14 wherein said converter means for converting the frequency change from the beginning to the end of said measurement interval to a corrosion thickness signal comprises means for generating an uncorrected incremental thickness signal prior to applying said corrective value, said incremental thickness signal being obtained by multiplying said temperature-corrected frequency measurements at the beginning and end of said measurement interval by a thickness conversion factor to obtain cumulative corrosion thickness values for the beginning and end of said measurement interval, and subtracting said cumulative corrosion thickness values to obtain said incremental thickness signal.

16. The apparatus of claim 12, further comprising:

means for monitoring the relative humidity in said corrosive atmosphere; and means for providing a warning signal indicating that corrosion in said atmosphere is related to humidity whenever said relative humidity exceeds a predetermined level or rises at greater than a predetermined rate, at the same time as said corrosion thickness signal for one of said measurement intervals exceeds a predetermined thickness.

17. The apparatus of claim 16, further comprising means for storing said corrected corrosion thickness signal.

18. The apparatus of claim 17, further comprising means for displaying said corrected corrosion thickness signal.

19. The apparatus of claim 18, further comprising means for measuring and displaying an indicia of the temperature condition at which said frequency measurements are made.

20. The apparatus of claim 19, wherein said corrodible substance is a metal selected from the group consisting of copper, silver, and nickel.

21. The apparatus of claim 19, wherein said corrodible substance is a gold-coated corrodible metal.

* * * * *